(12) United States Patent
Yamamoto

(10) Patent No.: US 10,451,049 B2
(45) Date of Patent: Oct. 22, 2019

(54) LIQUID CARBON DIOXIDE DELIVERY PUMP, AND SUPERCRITICAL FLUID CHROMATOGRAPH PROVIDED WITH THE SAME

(71) Applicant: SHIMADZU CORPORATION, Kyoto-shi, Kyoto (JP)

(72) Inventor: Shintaro Yamamoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/061,214

(22) Filed: Mar. 4, 2016

(65) Prior Publication Data

US 2016/0274071 A1    Sep. 22, 2016

(30) Foreign Application Priority Data

Mar. 18, 2015  (JP) ................................. 2015-054422

(51) Int. Cl.
*F04B 39/06* (2006.01)
*G01N 30/32* (2006.01)
(Continued)

(52) U.S. Cl.
CPC ............ *F04B 39/064* (2013.01); *F04B 15/06* (2013.01); *F04B 39/06* (2013.01); *G01N 30/30* (2013.01);
(Continued)

(58) Field of Classification Search
CPC .. F04B 15/06; F04B 2015/0818; F04B 39/06; F04B 39/064; G01N 30/32; G01N 30/36;
(Continued)

(56) References Cited

U.S. PATENT DOCUMENTS

| 4,155,683 A | 5/1979 | Mochizuki et al. |
| 4,597,943 A | 7/1986 | Sugiyama et al. |

(Continued)

FOREIGN PATENT DOCUMENTS

| CN | 102203421 A | 9/2011 |
| CN | 102879483 A | 1/2013 |

(Continued)

OTHER PUBLICATIONS

Office Action dated Feb. 2, 2018, issued in counterpart Chinese Application No. 201511021209.7 (5 pages).

(Continued)

*Primary Examiner* — Peter J Macchiarolo
*Assistant Examiner* — Irving A Campbell
(74) *Attorney, Agent, or Firm* — Westerman, Hattori, Daniels & Adrian, LLP

(57) ABSTRACT

A liquid carbon dioxide delivery pump with a pump head including a pump chamber and a refrigerant channel different from a channel passing through the pump chamber, a circulation channel for refrigerant, a refrigerant pump arranged on the circulation channel, the refrigerant pump for causing the refrigerant to circulate through the circulation channel, and a cooling section arranged on the circulation channel, at a position away from the pump head, the cooling section being configured to cool the refrigerant passing through the circulation channel. The liquid carbon dioxide delivery pump further has a temperature sensor for detecting an ambient temperature of the pump head or a temperature of the pump head, and a refrigerant pump control section for adjusting, based on a detection signal of the temperature sensor, a flow rate of the refrigerant pump such that liquid carbon dioxide flowing through the pump head at a specific temperature.

8 Claims, 4 Drawing Sheets

(51) Int. Cl.
    *F04B 15/06* (2006.01)
    *G01N 30/30* (2006.01)
    *F04B 15/08* (2006.01)
    *G01N 30/36* (2006.01)

(52) U.S. Cl.
    CPC ...... *G01N 30/32* (2013.01); *F04B 2015/0818* (2013.01); *G01N 30/36* (2013.01); *G01N 2030/326* (2013.01)

(58) Field of Classification Search
    CPC ... G01N 2030/326; G01N 30/30; B01D 15/08
    USPC .............................................. 62/3.2; 73/23.41
    See application file for complete search history.

(56) References Cited

U.S. PATENT DOCUMENTS

| | | | |
|---|---|---|---|
| 5,031,448 A | 7/1991 | Saito | |
| 5,635,070 A | 6/1997 | Allington et al. | |
| 5,704,276 A | 1/1998 | Osajima et al. | |
| 6,449,969 B1* | 9/2002 | Fujimoto | F24F 11/008 165/247 |
| 6,607,142 B1* | 8/2003 | Boggs | B60K 6/22 180/65.1 |
| 6,821,481 B1 | 11/2004 | Osajima et al. | |
| 9,766,214 B2 | 9/2017 | Goto et al. | |
| 2003/0215341 A1 | 11/2003 | Maiefski et al. | |
| 2009/0049891 A1* | 2/2009 | Shaimi | B01D 15/1864 73/23.36 |
| 2009/0099791 A1* | 4/2009 | Zettel | G01F 1/696 702/45 |
| 2011/0094606 A1 | 4/2011 | Kanomata et al. | |
| 2014/0190183 A1* | 7/2014 | Berger | F04B 39/064 62/3.2 |
| 2015/0330954 A1 | 11/2015 | Goto et al. | |
| 2016/0139092 A1 | 5/2016 | Dumas et al. | |
| 2016/0202218 A1 | 7/2016 | Owa | |

FOREIGN PATENT DOCUMENTS

| | | |
|---|---|---|
| CN | 203809238 U | 9/2014 |
| CN | 104297072 A | 1/2015 |
| EP | 2317310 A1 | 5/2011 |
| JP | 2002-227644 A | 8/2002 |
| WO | 03098046 A1 | 11/2003 |
| WO | 2012/122361 A2 | 9/2012 |
| WO | 2012122361 | 9/2012 |
| WO | 2014204843 A1 | 12/2014 |
| WO | 2014189738 A3 | 5/2015 |

OTHER PUBLICATIONS

Non-Final Office Action dated Dec. 20, 2017, issued in U.S. Appl. No. 15/041,404 (12 pages).

Office Action dated May 8, 2018, issued in counterpart Japanese Application No. 2015-054422, with English machine translation. (6 pages).

Office Action dated May 22, 2018, issued in Japanese Application No. 2015-054397 which is counterpart to U.S. Appl. No. 15/041,404; with English machine translation. (6 pages).

Office Action dated May 30, 2018, issued in counterpart Chinese Application No. 201511023539.X, with English translation. (14 pages).

Office Action dated Dec. 27, 2018, issued in counterpart Chinese application No. 201511023539.X, with English translation. (10 pages).

Non-Final Office Action dated Oct. 16, 2018, issued in U.S. Appl. No. 15/041,404. (12 pages).

Final Office Action dated Feb. 28, 2019, issued in U.S. Appl. No. 15/041,404 (12 pages).

* cited by examiner

LIQUID CARBON DIOXIDE DELIVERY PUMP, AND SUPERCRITICAL FLUID CHROMATOGRAPH PROVIDED WITH THE SAME

BACKGROUND OF THE INVENTION

1. Field of the Invention

The present invention relates to a supercritical fluid chromatograph, and a liquid carbon dioxide delivery pump used by the same.

2. Description of the Related Art

A supercritical fluid chromatograph (SFC) uses a supercritical fluid as a mobile phase. A typical example of a supercritical fluid is supercritical carbon dioxide. Supercritical carbon dioxide is carbon dioxide at or above a critical temperature or a critical pressure. Supercritical fluid chromatography most often uses carbon dioxide because its critical pressure is 7.38 MPa, its critical temperature is, at 31.1° C., relatively close to a normal temperature, and it is non-flammable and chemically unreactive, and highly pure carbon dioxide may be obtained at a low cost. Supercritical carbon dioxide has properties that are desirable for chromatography, namely, low viscosity and high diffusivity. Compared to liquid chromatography, supercritical carbon dioxide chromatography is expected to achieve fast and more desirable separation.

Supercritical carbon dioxide is non-polar, and is similar to n-hexane, and thus, supercritical fluid chromatography that uses supercritical carbon dioxide as a mobile phase is basically normal chromatography, and is suitable for analysis of a non-polar compound. However, supercritical carbon dioxide is compatible with polar organic solvents such as methanol and ethanol, and by adding such a polar organic solvent as a modifier, the mobile phase may be polarized, and analysis of a polar compound is enabled. Accordingly, gradient analysis in which the added proportion of a modifier is gradually increased over time is also performed.

According to a supercritical fluid chromatograph that uses supercritical carbon dioxide, liquid carbon dioxide is delivered by being pressurized by a delivery pump. As the delivery pump, a plunger pump, for example, having a plunger that reciprocates inside a pump chamber is used. The delivery pump is used being cooled to a temperature below the critical temperature, such as 5° C., so as to perform delivery in a state of liquid carbon dioxide.

With the delivery pump, to prevent a rise in the temperature due to generation of heat during pressurization of liquid carbon dioxide, a heat exchange block is attached to a pump head, and a pipe from a cooling water circulation device installed outside the device is connected to cool the heat exchange block by cooling water, or a cooling device, such as a Peltier device, is attached to the heat exchange block to cool the block (see WO 2012/122361 A2).

SUMMARY OF THE INVENTION

In the case of using a plunger pump as a delivery pump of liquid carbon dioxide, maintenance work, such as regularly exchanging a plunger or a plunger seal, becomes necessary. In the maintenance work, the plunger or the plunger seal has to be taken out by disassembling the pump head. However, if the heat exchange block is attached to the pump head, and a pipe or a cooling device is further attached, these members have to be removed/mounted at the time of the maintenance work, and the efficiency of the maintenance work is reduced.

Even if a pump other than the plunger pump is used as the delivery pump, if the maintenance work has to be performed by disassembling its pump head, such a case is a subject of the present invention.

The present invention has its object to increase the efficiency of maintenance work of a delivery pump, for delivering liquid carbon dioxide, of a supercritical fluid chromatograph and to maintain the temperature of the pump head at a specific temperature even when an ambient temperature of the pump head changes.

An embodiment of a liquid carbon dioxide delivery pump according to the present invention includes a pump head including a pump chamber for delivering liquid carbon dioxide and a refrigerant channel different from a liquid carbon dioxide channel passing through the pump chamber, a circulation channel for refrigerant including the refrigerant channel, a refrigerant pump that is arranged on the circulation channel, the refrigerant pump being for causing the refrigerant to circulate through the circulation channel, a cooling section that is arranged on the circulation channel, at a position away from the pump head, the cooling section being configured to cool the refrigerant passing through the circulation channel, a temperature sensor for detecting an ambient temperature of the pump head or a temperature of the pump head, and a refrigerant pump control section for adjusting, based on a detection signal of the temperature sensor, a flow rate of the refrigerant pump so that liquid carbon dioxide flowing through the pump head is at a specific temperature.

An embodiment of a supercritical fluid chromatograph according to the present invention includes the liquid carbon dioxide delivery pump of the present invention, a modifier supply channel for supplying a modifier to a mobile phase channel to which liquid carbon dioxide is supplied by the liquid carbon dioxide delivery pump, a sample injection section for injecting a sample into an analysis channel at a downstream of a merging section of the mobile phase channel and the modifier supply channel, a separation column that is arranged at a downstream of the sample injection section, a back pressure valve that is arranged at a downstream of the separation column, the back pressure valve for maintaining a pressure at which a mobile phase in the separation column is in a supercritical fluid state, and a detector that is arranged between the separation column and the back pressure valve, or at a downstream of the back pressure valve.

According to an embodiment of the present invention, a heat exchange block is not attached to a pump head of a delivery pump. Instead, a refrigerant channel exchanges heat with the pump head and cools a pump chamber. Since a heat exchange block is not attached as in a conventional case, the maintenance work of the pump head is facilitated.

Further, since the ambient temperature of the pump head or a temperature of the pump head is detected by the temperature sensor, and the flow rate of the refrigerant pump is adjusted based on the detection signal of the temperature sensor so that the liquid carbon dioxide flowing through the pump head is at a specific temperature, the temperature of the pump head is maintained at a specific temperature even when an ambient temperature of the pump head changes.

DETAILED DESCRIPTION OF THE INVENTION

Figure 1:
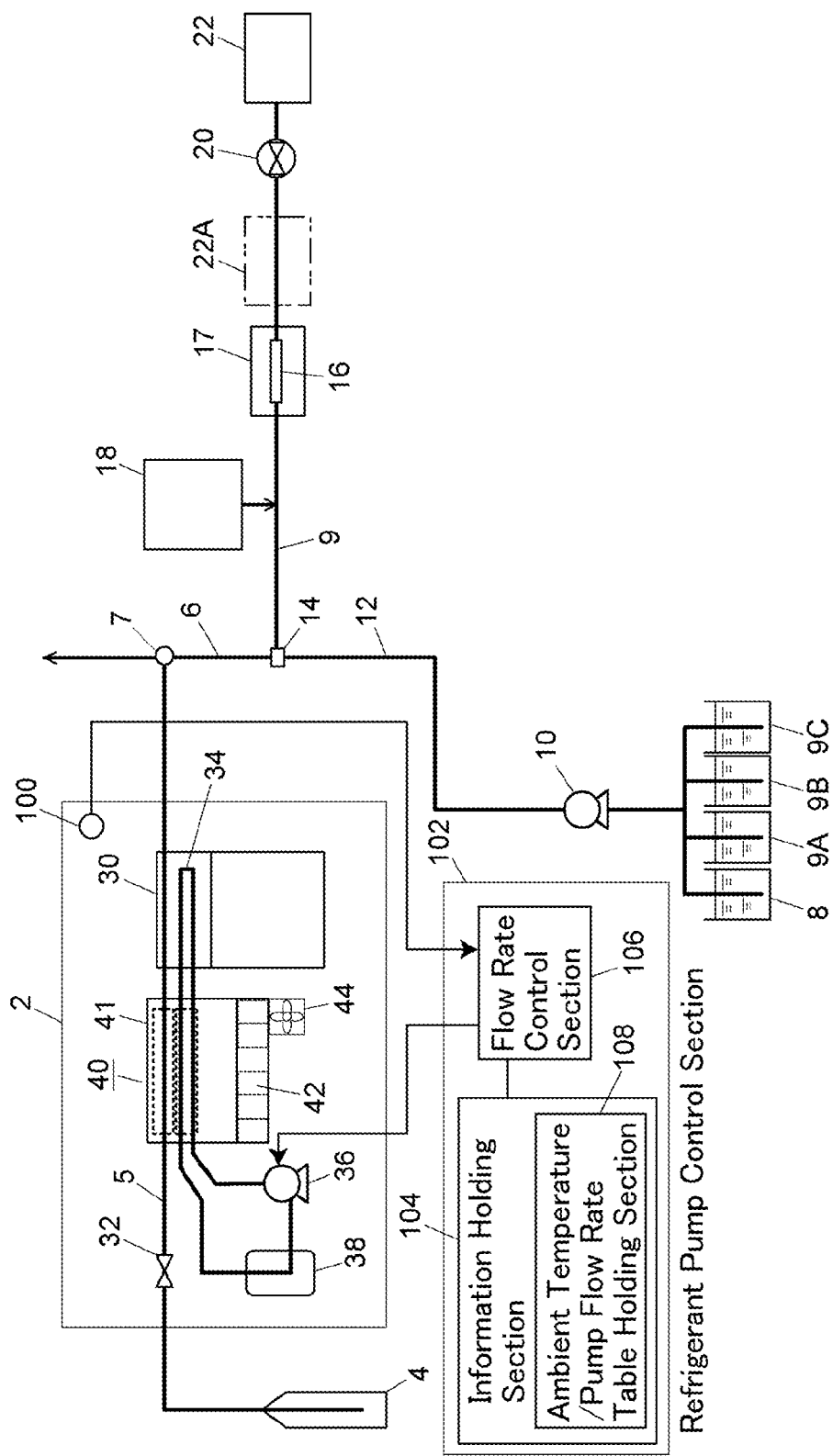
FIG. 1 is a schematic configuration diagram showing a supercritical fluid chromatograph according to an example.

FIG. 1 schematically shows a supercritical fluid chromatograph of an example. A delivery pump 2 pressurizes liquid carbon dioxide from a liquid carbon dioxide container 4, and supplies the same to a mobile phase channel 6. The liquid carbon dioxide container 4 may be a cylinder containing liquid carbon dioxide, or a tank that generates liquid carbon dioxide by cooling supplied carbon dioxide gas, and that contains the liquid carbon dioxide.

A modifier supply channel 12 for supplying a modifier 8, which is a highly polar solvent such as methanol, by a pump 10 is connected to the mobile phase channel 6.

A separation column 16 is arranged on an analysis channel 9 at the downstream of a merging point 14 of the mobile phase channel 6 and the modifier supply channel 12. The separation column 16 is contained inside a column oven 17 in such a way that the temperature is made constant. A sample injection section 18, such as an automatic sample injection device (autosampler) or the like, for injecting a sample into the analysis channel 9 between the merging point 14 and the separation column 16 is arranged. To maintain the pressure inside the analysis channel 9, a back pressure valve (BPR) 20 is arranged at the downstream of the separation column 16. The pressure of the back pressure valve 20 and the temperature of the column oven 17 are set in such a way that the mobile phase inside the analysis channel 9 is in a supercritical state at least inside the separation column 16.

A detector 22 for detecting a sample component separated by the separation column 16 is arranged. Although not specifically limited, a mass spectrometer, such as a tandem quadrupole mass spectrometer, is used as the detector 22 in the present example. A mass spectrometer as the detector 22 includes an ESI (electrospray ionization) source. A mobile phase is in a supercritical state in the analysis channel 9 on the upstream side of the back pressure valve 20, but on the downstream side of the back pressure valve 20, the mobile phase is discharged to an atmospheric pressure, and thus, sample components separated and eluted by the column 16 are discharged as a mist, together with the mobile phase, on the downstream side of the back pressure valve 20. When a voltage (electrospray voltage) is applied to between a discharge port of the mobile phase and an ionization chamber of the mass spectrometer, the eluted sample components are ionized and are analyzed by the mass spectrometer.

In the case of using the mass spectrometer as the detector 22, an ionization accelerator, such as formic acid or ammonia, may be added to a mobile phase to accelerate ionization of a sample component in the ionization chamber of the mass spectrometer. Further, a make-up solution as an ionization support agent may be supplied by a pump to an analysis channel between the column 16 and the back pressure valve 20. As the make-up solution, a solution obtained by including an ionization support agent, such as formic acid or ammonia, in an organic solvent, such as methanol, or water may be used.

As the detector, a detector 22A such as an ultraviolet-visible spectrophotometer may be arranged between the separation column 16 and the back pressure valve 20. Such a detector 22A may be provided instead of the detector 22 that is arranged at the downstream of the back pressure valve 20, or may be provided together with the detector 22 that is arranged at the downstream of the back pressure valve 20.

Furthermore, a detector 22A such as an ultraviolet-visible spectrophotometer may be arranged between the separation column 16 and the back pressure valve 20, and a fraction collector may be connected at the downstream of the back pressure valve 20, and the operation of the fraction collector may be controlled based on a detection signal of the detector 22A.

A relief valve 7 is provided to the mobile phase channel 6 so as to prevent the pressures inside the mobile phase channel 6 and the analysis channel 9 from reaching or exceeding a withstanding pressure. The relief valve 7 may be set to be released at a specific pressure of, for example, 45 MPa or 60 MPa.

When analysis is not being performed, washing liquids 9A to 9C may be supplied by the pump 10 into the channel of the supercritical fluid chromatograph so as to wash the channel. Although not shown in the drawing, a channel switching valve is provided between the pump 10, and the channels for the modifier 8 and the washing liquids 9A to 9C so that one of the modifier 8 and the washing liquids 9A to 9C may be selected and be supplied by the pump 10.

A behavior of liquid carbon dioxide at the supercritical fluid chromatograph will be described. Liquid carbon dioxide is assumed to be contained in a cylinder 4, and its pressure is, for example, 7 MPa. The back pressure valve 20 is controlled to be at a specific pressure between 10 MPa and 41 MPa so that the pressure inside the analysis channel is, for example, 20 MPa to 25 MPa inside the separation column 16 and liquid carbon dioxide is supercritical carbon dioxide at least inside the separation column 16. In gradient analysis, the pressure at the separation column 16 is increased due to the proportion of a modifier in the supercritical carbon dioxide gradually increasing over time.

Next, the delivery pump 2 will be described. The delivery pump 2 is for delivering liquid carbon dioxide by a plunger pump head 30. The delivery pump 2 has the pump head 30 cooled to a temperature below the critical temperature of carbon dioxide, such as 5° C., so as to deliver the liquid carbon dioxide from the cylinder 4 in a liquid state, and the liquid carbon dioxide is delivered to the mobile phase channel 6 while being pressurized to, for example, 20 MPa so that it will be in a supercritical state when the mobile phase is heated to or above the critical temperature of carbon dioxide at the downstream of the pump head 30.

An on-off valve 32 is arranged on a channel 5 for the liquid carbon dioxide extending from the cylinder 4 to the pump head 30. The withstanding pressure of the on-off valve 32 is, for example, 7.4 MPa. Although a control circuit of the on-off valve 32 is not shown in the drawing, the on-off valve 32 is controlled to open or close in synchronization with the timing of on/off of the pump head 30 so as to cause the liquid carbon dioxide to flow only when the pump head 30 is operating (on).

To remove heat that is generated by a discharge operation by the plunger of the pump head 30 and maintain a specific temperature of the pump head 30 (in the present example, 5° C.), a channel 34 for refrigerant through which a cooled refrigerant is to flow is provided to the pump head 30. The channel 34 is a circulation channel through which the refrigerant is made to circulate by a pump 36. A diaphragm pump, for example, may be used as the pump 36. A tank 38 for refrigerant is arranged on the channel 34. As the refrigerant, non-volatile ethylene glycol, for example, is used. However, other refrigerants may also be used.

In order to cool a refrigerant circulating through the channel 34, the channel 34 is arranged in such a way as to contact a cooling block 41 of a cooling section 40 and to penetrate the cooling block 41. A refrigerant flowing through the channel 34 is cooled by the cooling block 41. The cooling block 41 includes a Peltier device as a cooling device. The part indicated by a reference numeral 42 indicates the Peltier device and its heat sink fins, and a fan 44 for sending air to the heat sink fins to radiate the heat of the heat sink fins is provided. The cooling section 40 includes the Peltier device and heat sink fins 42, the cooling block 41, and the fan 44.

The channel 5 for liquid carbon dioxide extending from the cylinder 4 to the pump head 30 is arranged in such a way that the downstream part of the on-off valve 32 contacts and penetrates the cooling block 41. According to such a structure, liquid carbon dioxide up to the pump head 30 is also cooled by the cooling block 41 of the cooling section 40.

With the delivery pump 2, liquid carbon dioxide is adiabatically compressed and pressurized by the pump head 30, and heat generated at this time is absorbed by the refrigerant flowing through the channel 34 and is radiated.

A structure for maintaining the temperature of liquid carbon dioxide flowing through the pump head 30 at a specific temperature (in the present example, 5° C.) even when the ambient temperature of the pump head 30 changes will be described.

A temperature sensor 100 for detecting the ambient temperature of the pump head 30 or the temperature of the pump head 30 is provided. As the temperature sensor 100, a thermocouple, a resistance thermometer, and various others may be used. A refrigerant pump control section 102 is provided for adjusting, based on a detection signal of the temperature sensor 100, the flow rate of the refrigerant pump 36 so that the liquid carbon dioxide flowing through the pump head 30 is at a specific temperature.

The refrigerant pump control section 102 may be realized by a dedicated computer of the delivery pump 2, a dedicated computer of a supercritical fluid chromatograph which uses the delivery pump 2, or a general-purpose personal computer. Moreover, the refrigerant pump control section 102 may also be configured by an electronic circuit.

According to an embodiment, the temperature sensor 100 is installed to detect the ambient temperature of the pump head 30. In this case, the refrigerant pump control section 102 includes an information holding section 104 holding information that is obtained in advance as a relationship between the ambient temperature of the pump head 30 and the flow rate of the refrigerant pump 36 when the temperature of liquid carbon dioxide flowing through the pump head 30 becomes constant, and a flow rate control section 106 for adjusting the flow rate of the refrigerant pump 36 based on the information held in the information holding section 104 and a detection signal of the temperature sensor 100. An example of the information held in the information holding section 104 is a table showing a relationship between the ambient temperature and the pump flow rate. In this case, the information holding section 104 is an ambient temperature/pump flow rate table holding section 108 that holds the information as a table.

In another embodiment, the temperature sensor 100 is installed to detect the temperature of the pump head 30. In this case, the refrigerant pump control section 102 includes the flow rate control section 106 for performing feedback control of the flow rate of the refrigerant pump 36 so that the detected temperature of the temperature sensor 100 becomes constant.

Figure 2:
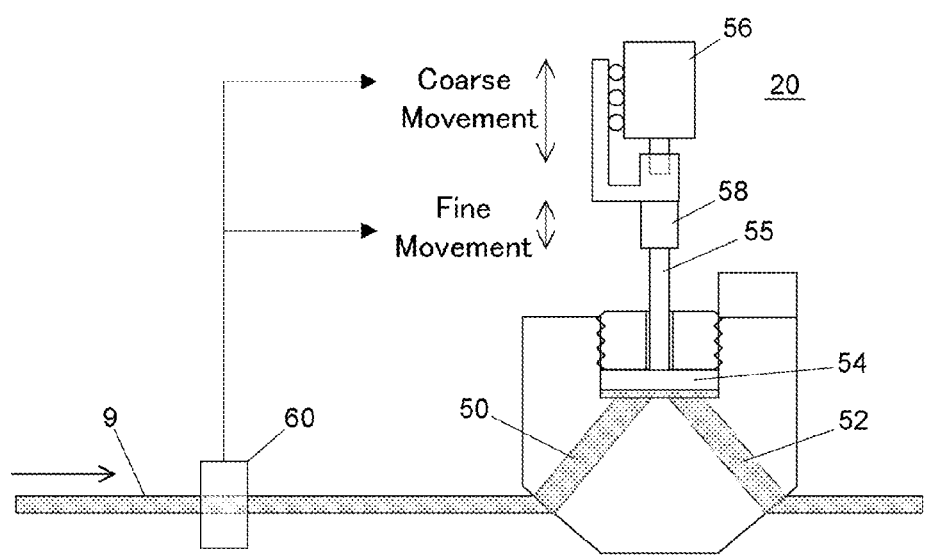
FIG. 2 is a schematic cross-sectional diagram showing an example of a back pressure valve of the supercritical fluid chromatograph.

FIG. 2 shows an example of the back pressure valve 20. At the back pressure valve 20, the connection between a channel 50 that is joined to the analysis channel 9 and a channel 52 that is open to the atmosphere is adjusted by a valve 54. The size of the gap between that valve 54 and a seat where the opening of the channel 50 and the opening of the channel 52 are provided is adjusted, and a pressure that is generated by the channel resistance according to the size of the gap is the pressure on the upstream side of the back pressure valve 20. An actuator 55 for moving the valve 54 in the direction of the seat is driven by a stepper motor 56 and a piezo element 58, and the gap between the seat and the valve 54 is adjusted. The stepper motor 56 is used when moving the actuator 55 in a wide range, and the piezo element 58 is used when moving the actuator 55 in a narrow range. A pressure sensor 60 is provided to the analysis channel 9, and the actuator 55 is driven by the stepper motor 56 and the piezo element 58 in such a way that detection signals of the pressure sensor 60 are constant.

Figure 3:
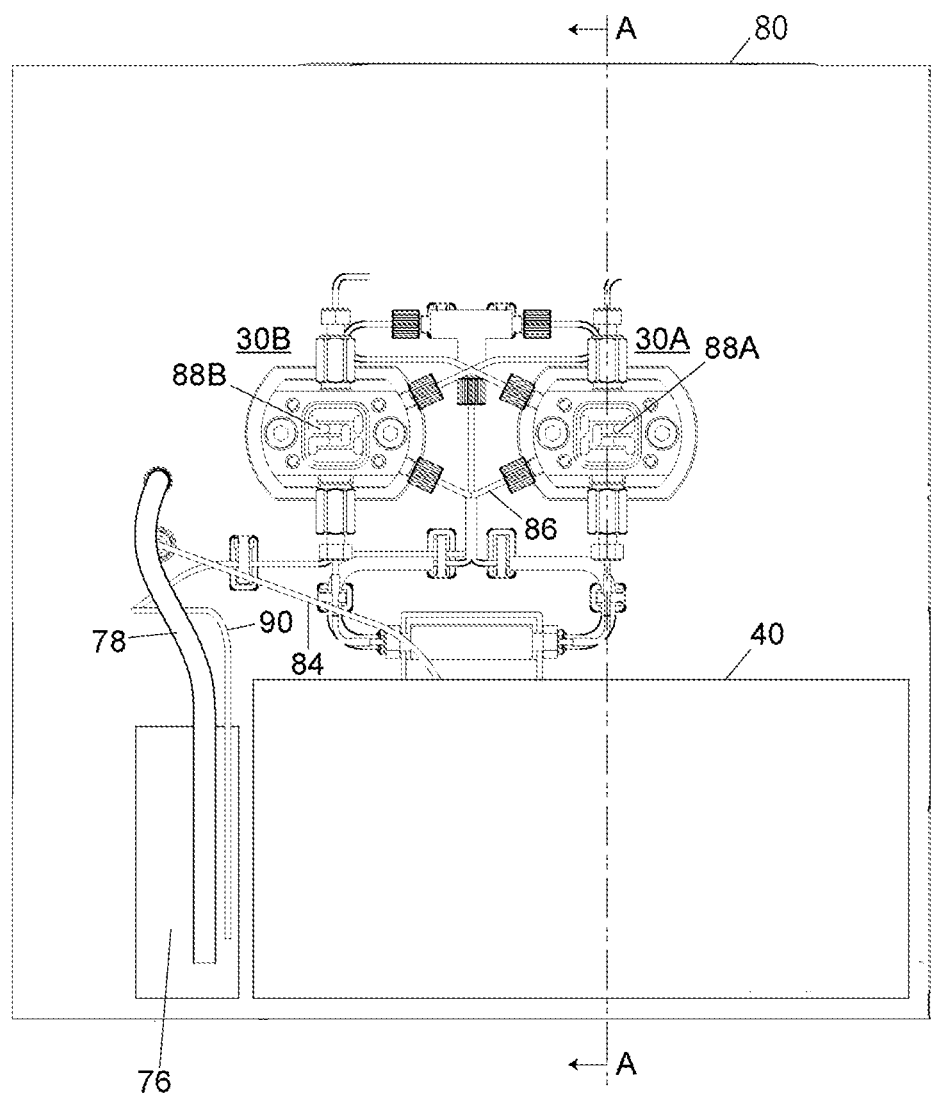
FIG. 3 is a front view showing main sections of a delivery pump of an example in a state where a pump head is removed.
Figure 4:
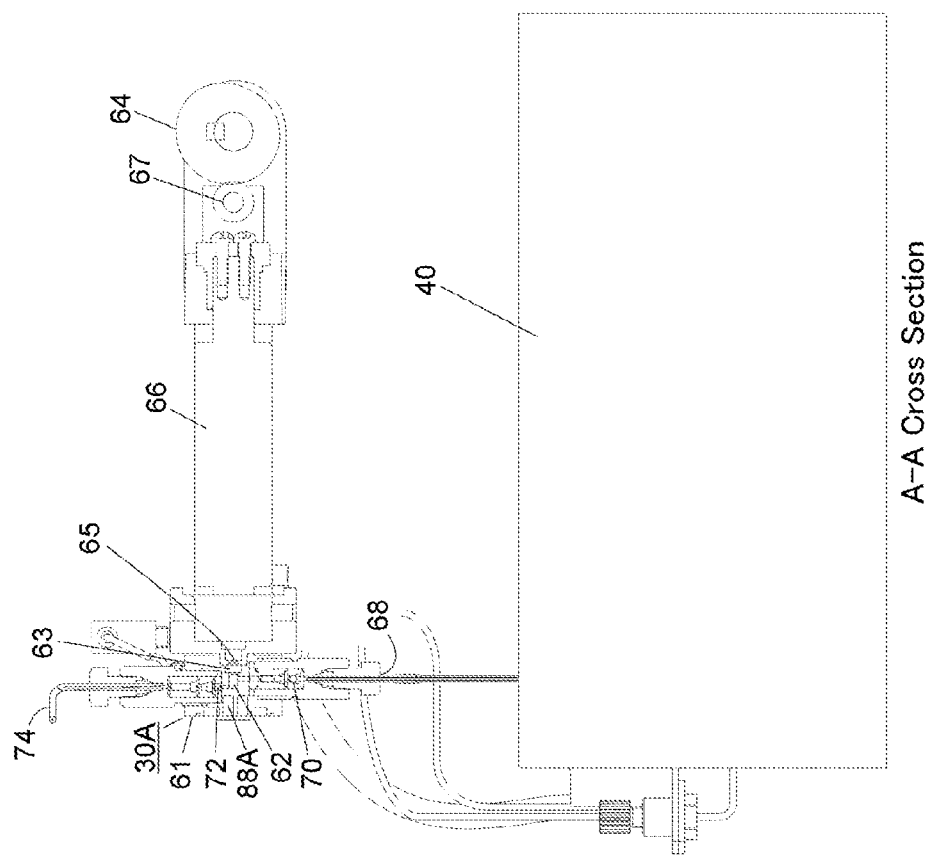
FIG. 4 is a cross-sectional diagram along line A-A in FIG. 3.

A concrete structure of the delivery pump 2 is shown in FIGS. 3 and 4. In the present example, two plunger pump heads 30A and 30B are included, and channels on their outlet sides are merged. The two pump heads 30A and 30B are driven at different phases so that the pulsation of the flow rate of merged liquid carbon dioxide is made small.

FIG. 3 shows, with respect to the pump heads 30A and 30B, a state where lids 61 forming channels 88A and 88B through which refrigerants flow are removed. The side where the lids 61 are is the front side of the delivery pump, and plungers 65 are arranged on the opposite back side.

First, the structures of the pump heads 30A and 30B for supplying liquid carbon dioxide will be described. Since the structures of the pump heads 30A and 30B are the same, the pump head 30A will be described with reference to FIG. 4. The pump head 30A performs delivery by the plunger 65, sealed in a liquid-tight manner by a plunger seal 63, reciprocating inside a pump chamber 62. The plunger 65 is arranged at a tip end of a rod 66, and the plunger 65 is driven to reciprocate inside the pump chamber 62 by the rod 66, by a cam follower 67 at a base end section of the rod 66 abutting a cam 64 and the cam 64 being rotated by a motor (not shown). A channel 68 for supplying liquid carbon dioxide is connected to the inlet of the pump chamber 62 via a check valve 70, and a channel 74 on the outlet side is connected to the outlet of the pump chamber 62 via a check valve 72. Liquid carbon dioxide is supplied from the channel 68 into the pump chamber 62, pressurized in the pump chamber 62 and delivered out into the channel 74 by the reciprocation of the plunger 65 inside the pump chamber 62 and the actions of the check valves 70 and 72.

Next, a circulation channel for refrigerant will be described. A refrigerant tank accommodation section 76 is provided in order to install a refrigerant tank 38 (see FIG. 1). To cause the refrigerant in the refrigerant tank 38 installed inside the refrigerant tank accommodation section 76 to circulate, a tip end of a tube 78 for suctioning the refrigerant by a pump (not shown) is arranged at a position where it is inserted in the refrigerant tank 38. The tube 78 is joined to a channel 84 formed of a metal pipe via the aforementioned pump, and the channel 84 is arranged to pass through the cooling block 41 (see FIG. 1) of the cooling section 40. The cooling block 41 is arranged at a position away from the pump heads 30A and 30B, and in the present example, it is arranged below the pump heads 30A and 30B. The pipe forming the channel 84 is made of metal such as stainless steel, and inside the cooling block 41, it is in contact with the cooling block 41 via a thermal conductive member. The cooling block 41 is made of high thermal conductivity metal such as aluminum. In this manner, the channel 84 and the cooling block 41 are structured so that heat is satisfactorily exchanged. As shown in FIG. 3, the channel 84 which has passed through the cooling block 41 is joined, via a channel 86 formed of a metal pipe to the channels 88A and 88B for refrigerant provided respectively to the pump heads 30A and 30B. The pump heads 30A and 30B are made of high thermal conductive metal such as stainless steel. The channels 88A and 88B are meandering channels provided at positions, inside the pump heads 30A and 30B, adjacent to the pump chamber 62, and exchange heat with the pump chamber 62 inside the pump heads 30A and 30B. The channels 88A and 88B merge with a channel 90 formed of one pipe via respective outlet channels, and the outlet of the channel 90 is arranged at a position where it is inserted in the refrigerant tank 38 installed inside the refrigerant tank accommodation section 76, and the refrigerant from the channel 90 is returned to the refrigerant tank 38.

The materials of the tube 78 and the channel 90 are not particularly limited, but are desirably flexible materials, such as fluoro resin, so as to facilitate insertion into the refrigerant tank 38 at the refrigerant tank accommodation section 76.

As described, the tube 78, the channel 84, the channel 86, the channels 88A and 88B, and the channel 90 form the circulation channel 34 shown in FIG. 1. A refrigerant is suctioned by the tube 78 from the refrigerant tank 38, is cooled by the cooling block 41 while flowing through the channel 84 and is led to the pump heads 30A and 30B, and cool the pump heads 30A and 30B. The refrigerants which have flowed through the pump heads 30A and 30B are returned to the refrigerant tank 38 via the channel 90, suctioned again by the tube 78, and are used to cool the pump heads 30A and 30B.

A member which would interfere with the maintenance work of the pump heads 30A and 30B, such as the cooling block 41, is not arranged at the front sides of the pump heads 30A and 30B. The cooling section 40 including the cooling block 41 is arranged at a position away from the pump heads 30A and 30B, and in this example, it is arranged below the pump heads 30A and 30B. The pump heads 30A and 30B are cooled not by the cooling block 41 itself, but by a refrigerant that is cooled by the cooling block 41, and thus, the cooling block 41 may be arranged at a position away from the pump heads 30A and 30B by connecting the cooling block 41 and the pump heads 30A and 30B by channels for refrigerant.

Although not shown in FIGS. 3 and 4, the pump 36 for refrigerant circulation is arranged at a side of the pump for delivery of liquid carbon dioxide including the pump heads 30A and 30B. In this manner, both the cooling block 41 and the pump 36 are arranged at positions away from the position in front of the pump heads 30A and 30B. With the pump for delivery of liquid carbon dioxide, the plunger seal 63 and the plunger 65 may be removed by removing the lids 61 forming the channels for refrigerant and also by removing the pump heads 30A and 30B to the front side. Compared to a conventional structure where the cooling block is attached to the pump head, the maintenance work of the pump for delivery of liquid carbon dioxide is easy.

The channel 68 for supplying liquid carbon dioxide is also made of high thermal conductive metal, and in the same way as the channel 84 for refrigerant, it is configured to pass through the cooling block 41 and be cooled by being in contact with the cooling block 41 in a manner capable of exchanging heat. Liquid carbon dioxide generates heat by adiabatic compression at the time of being pressurized by the pump heads 30A and 30B, and thus, by cooling liquid carbon dioxide to be led to the pump heads 30A and 30B by a cooling unit 82, the liquid carbon dioxide to be delivered out from the pump heads 30A and 30B may be easily maintained at a predetermined temperature.

Almost the entire delivery pump 2 is accommodated inside a housing 80, and to facilitate maintenance and operation, the pump heads 30A and 30B, and the refrigerant tank accommodation section 76 are arranged being exposed to the front side from a front panel of the housing 80.

What is claimed is:

1. A liquid carbon dioxide delivery pump comprising:
    a plunger pump head configured to deliver liquid carbon dioxide, wherein a refrigerant channel is provided inside the plunger pump head and is different from a channel in which liquid carbon dioxide flows;
    a circulation channel for refrigerant including the refrigerant channel;
    a refrigerant pump that is arranged on the circulation channel, the refrigerant pump being for causing the refrigerant to circulate through the circulation channel;
    a cooling section that is arranged on the circulation channel, at a position away from the pump head, the cooling section being configured to cool the refrigerant passing through the circulation channel;
    a temperature sensor for detecting an ambient temperature of the pump head or a temperature of the pump head; and
    a refrigerant pump control section for adjusting, based on a detection signal of the temperature sensor, a flow rate of the refrigerant pump such that liquid carbon dioxide flowing through the pump head is at a specific temperature.

2. The liquid carbon dioxide delivery pump according to claim 1,
    wherein the temperature sensor is installed to detect the ambient temperature of the pump head, and
    wherein the refrigerant pump control section includes
        an information holding section holding information that is obtained in advance as a relationship between the ambient temperature of the pump head and the flow rate of the refrigerant pump when a temperature of liquid carbon dioxide flowing through the pump head becomes constant, and
        a flow rate control section for adjusting the flow rate of the refrigerant pump based on the information held in the information holding section and a detection signal of the temperature sensor.

3. The liquid carbon dioxide delivery pump according to claim 2, wherein the information holding section is an ambient temperature/pump flow rate table holding section that holds 5 the information as a table.

4. The liquid carbon dioxide delivery pump according to claim 1,
    wherein the temperature sensor is installed to detect the temperature of the pump head, and
    wherein the refrigerant pump control section includes a flow rate control section for performing feedback control of the flow rate of the refrigerant pump so that a detected temperature of the temperature sensor becomes constant.

5. A supercritical fluid chromatograph comprising:
    a liquid carbon dioxide delivery pump comprising, a plunger pump head configured to deliver liquid carbon dioxide, wherein a refrigerant channel is provided inside the plunger pump head and is different from a channel in which liquid carbon dioxide flows, a circulation channel for refrigerant including the refrigerant channel, a refrigerant pump that is arranged on the circulation channel, the refrigerant pump being for causing the refrigerant to circulate through the circulation channel, a cooling section that is arranged on the circulation channel, at a position away from the pump head, the cooling section being configured to cool the refrigerant passing through the circulation channel, a temperature sensor for detecting an ambient temperature of the pump head or a temperature of the pump head, and a refrigerant pump control section for adjusting, based on a detection signal of the temperature sensor, a flow rate of the refrigerant pump so that liquid carbon dioxide flowing through the pump head is at a specific temperature;

a modifier supply channel for supplying a modifier to a mobile phase channel to which liquid carbon dioxide is supplied by the liquid carbon dioxide delivery pump;

a sample injection section for injecting a sample into an analysis channel at a downstream of a merging section of the mobile phase channel and the modifier supply channel;

a separation column that is arranged at a downstream of the sample injection section;

a back pressure valve that is arranged at a downstream of the separation column, the back pressure valve for maintaining a pressure at which a mobile phase in the separation column is in a supercritical fluid state; and a detector that is arranged between the separation column and the back pressure valve, or at a downstream of the back pressure valve.

6. The supercritical fluid chromatograph according to claim 5, wherein the temperature sensor is installed to detect the ambient temperature of the pump head, and wherein the refrigerant pump control section includes an information holding section holding information that is obtained in advance as a relationship between the ambient temperature of the pump head and the flow rate of the refrigerant pump when a temperature of liquid carbon dioxide flowing through the pump head becomes constant, and a flow rate control section for adjusting the flow rate of the refrigerant pump based on the information held in the information holding section and a detection signal of the temperature sensor.

7. The supercritical fluid chromatograph according to claim 6, wherein the information holding section is an ambient temperature/pump flow rate table holding section that holds the information as a table.

8. The supercritical fluid chromatograph according to claim 5, wherein the temperature sensor is installed to detect the temperature of the pump head, and wherein the refrigerant pump control section includes a flow rate control section for performing feedback control of the flow rate of the refrigerant pump so that a detected temperature of the temperature sensor becomes constant.

* * * * *